US012599729B2

(12) United States Patent
Wieden

(10) Patent No.: US 12,599,729 B2
(45) Date of Patent: Apr. 14, 2026

(54) PERSONAL CONTAINER WITH ATTACHMENT MECHANISM

(71) Applicant: Robert Wieden, Eagan, MN (US)

(72) Inventor: Robert Wieden, Eagan, MN (US)

(73) Assignee: Robert Wieden, Eagan, MN (US)

( * ) Notice: Subject to any disclaimer, the term of this patent is extended or adjusted under 35 U.S.C. 154(b) by 834 days.

(21) Appl. No.: 17/885,354

(22) Filed: Aug. 10, 2022

(65) Prior Publication Data

US 2023/0047074 A1    Feb. 16, 2023

Related U.S. Application Data

(60) Provisional application No. 63/231,939, filed on Aug. 10, 2021.

(51) Int. Cl.
| | |
|---|---|
| *A61M 15/00* | (2006.01) |
| *A61M 11/00* | (2006.01) |
| *A62B 9/02* | (2006.01) |
| *A62B 18/02* | (2006.01) |
| *B65D 23/12* | (2006.01) |
| *B65D 47/08* | (2006.01) |
| *B65D 51/24* | (2006.01) |

(52) U.S. Cl.
CPC .......... *A61M 15/009* (2013.01); *A61M 11/00* (2013.01); *A62B 9/02* (2013.01); *A62B 18/02* (2013.01); *B65D 23/12* (2013.01); *B65D 47/089* (2013.01); *B65D 51/24* (2013.01)

(58) Field of Classification Search
CPC .. A61M 11/00; A61M 11/006; A61M 11/007; A61M 11/008; A61M 11/02; A61M 11/06; A61M 13/00; A61M 15/00; A61M 15/0001; A61M 15/0021; A61M 15/002; A61M 15/30025; A61M 15/0026; A61M 15/0086; A61M 15/009; A61M 15/06; A61M 15/08; A61M 15/085; B65D 23/12; B65D 47/089; B65D 47/0876; B65D 51/24
USPC ..................................................... 128/202.15
See application file for complete search history.

(56) References Cited

U.S. PATENT DOCUMENTS

| | | | | |
|---|---|---|---|---|
| 4,669,461 A * | 6/1987 | Battaglia | ............... | A61M 16/06 |
| | | | | 128/202.13 |
| 4,771,769 A * | 9/1988 | Hegemann | .......... | B05B 11/0032 |
| | | | | 128/200.22 |

(Continued)

*Primary Examiner* — Colin W Stuart
(74) *Attorney, Agent, or Firm* — Merchant & Gould P.C.

(57) ABSTRACT

A container for storing and dispensing a liquid and a gas to a user has a portable liquid container; a dual-purpose lid cover hingedly connected to the portable liquid container; a liquid dispensing cap attached to an upper portion of the portable liquid container; a nose cavity portion disposed on the dual-purpose lid cover to facilitate delivery of a gas; wherein said dual-purpose cap pivots from a secure liquid cap orientation to a gas delivery orientation. Also included is a a gas canister disposed on the portable liquid container. A valve assembly is disposed between the dual-purpose lid cover and the gas container wherein the gas is selectively dispensed and regulated through the dual-purpose lid cover when placed in the gas delivery orientation. Also provided is an attachment means for removably connecting said gas canister to said side of said portable liquid container.

15 Claims, 22 Drawing Sheets

(56)                    References Cited

U.S. PATENT DOCUMENTS

| | | | | |
|---|---|---|---|---|
| 6,526,966 | B1 * | 3/2003 | Peesay ................. | A61M 16/06 |
| | | | | 128/203.29 |
| 7,178,523 | B2 | 2/2007 | Sundhar | |
| 2001/0030271 | A1 * | 10/2001 | Weesner ............... | A61M 5/008 |
| | | | | 248/230.8 |
| 2003/0010337 | A1 * | 1/2003 | Anderson ........... | A61M 15/009 |
| | | | | 128/200.23 |
| 2006/0137683 | A1 * | 6/2006 | Anderson ............. | A61M 15/08 |
| | | | | 128/200.14 |
| 2014/0102463 | A1 * | 4/2014 | Jones ................... | A61M 15/06 |
| | | | | 131/329 |
| 2014/0291414 | A1 * | 10/2014 | Bretillot ............. | B05B 17/0615 |
| | | | | 239/102.2 |
| 2020/0163375 | A1 * | 5/2020 | Ubakar .................... | A24F 3/00 |
| 2021/0316900 | A1 * | 10/2021 | Burt ....................... | B65D 23/12 |
| 2022/0370250 | A1 * | 11/2022 | Oldakowski ............ | A61F 11/00 |
| 2022/0408949 | A1 * | 12/2022 | Durschlag .......... | B65D 81/3283 |

* cited by examiner

1400

2000

2200

PERSONAL CONTAINER WITH ATTACHMENT MECHANISM

RELATED APPLICATION

This application claims priority and herein incorporates by reference U.S. provisional patent application No. 63/231, 393 filed Aug. 10, 2021

FIELD OF INVENTION

The invention relates to a personal liquid container or bottle that combines a liquid compartment and a method incorporated to enable the attachment of other kinds of accessory containers including a portable gas canister to provide for a means to deliver inhalable gas. The bottle can include a dual-purpose lid cover that when pivoted from the liquid side dispensing cap turns into a contoured nasal gas delivery apparatus. In another embodiment of the invention, the detachable portable gas canister housing incorporates a nasal gas delivery apparatus. The present invention allows a user to drink a liquid and take nasal inhalations of purified gas in a safe and convenient manner, and which also enables the ability to attach and detach other accessories to a water bottle for utility and convenience.

BACKGROUND OF INVENTION

In the last two decades bottled water has become the leading consumer beverage product around the world. Consumers have shown that they are willing to purchase water for the convenience and the perceived purity of the bottled water. It should not be surprising since it addresses a basic human need and in a form factor that is easy to use. The buying decisions of these consumers are highly influenced by busy lifestyles and rapid urbanization.

Concerns over the alarming rise in plastic waste, has initiated various movements aimed at curtailing its use. The ongoing war against plastic is causing consumers to shift away from single-use water bottles towards reusable water bottles. For example, around 22 billion single-use plastic bottles are thrown out in the U.S. every year—enough to circle the earth four times—additionally, every hour, we throw away 2.5 million plastic bottles. Couple that with the fact that around 60 million plastic bottles end up in landfills every single day, which equates to sending more than 38 billion water bottles to landfills every year, the equivalent of 912 million gallons of oil. That means that 1,500 plastic bottles are thrown away every second of the day in the U.S. alone. These alarming numbers explain the need to reduce plastic waste and increase the adoption of reusable water bottles. It is not just the mounting plastic waste, but the amount of oil used in creating disposable plastic bottles that has encouraged manufacturers to shift their focus towards the production of reusable water bottles. In a bid to build a differentiated brand identity, manufacturers are launching innovative reusable water bottles that offer sustainability and are easy to carry. Manufacturers are thriving on the back of product innovation, as it helps them cater to a large pool of consumers with varied needs and preferences. The invention explained herein is an innovative product addressing this need.

In recent years, there has been a very noticeable shift in the thinking of a large majority of consumers on how one should live their life. Scientific research has bombarded people with a plethora of facts on why it is so important to monitor what is put into the body. As a result, there is a major trend showing consumers spending more and more money on products that are good for their bodies and promote a healthy lifestyle.

Furthermore, people today are becoming wary of the contaminants in the air they breathe and the effects it has on their health. In relation, it is easy to see the correlation between the unpolluted and polluted environments where people live. The normal atmospheric air in a clean and unpolluted environment is usually made up of 21% Oxygen ($O_2$), 78% Nitrogen ($N_2$) and 1% Carbon Dioxide ($CO_2$), Argon and various other gases. However, normal atmospheric air in polluted environments in which most of us live, such as most capital cities in the U.S., contain much higher levels of dangerous pollutants including Carbon Monoxide (CO), Lead (Pb), Nitrogen Dioxide ($NO_2$), Ozone ($O_3$) Particulate Matter (PM) and Sulfur Dioxide ($SO_2$). With pollution and greenhouse gases continuing to climb, consumers will demand a convenient, portable and affordable air quality solution, elevating the invention described herein as a necessary consumer product.

With the increase in interest in outdoor activities and health, and a coincidental decrease in air quality, a market has developed for pure oxygen. Breathing pure oxygen has time-established health benefits, as evidenced by its widespread use in hospitals, and is a proven way to increase alertness and athletic performance.

Heretofore, however, pure oxygen is typically administered to a user via a heavy, high-pressure tank and a face mask. The user wheels the high-pressure tank around and is encumbered thereby. If a patient requires constant oxygen, high pressure tanks are necessary in order to administer the thousands of daily breaths a patient consumes. However, in the case of an athlete or health enthusiast desiring only a few breaths as a supplement, a heavy tank is neither necessary nor desired.

In return, water plays an important role in nearly every major function in the body including body temperature, carrying nutrients and oxygen to cells, removing waste, cushioning joints and protecting organs and tissues. It also makes up 60% of a person's body weight and is the number one concern on any active person's intake list. For both performance and health, the importance of your water intake exceeds that of your vitamin, calorie and electrolyte intake. In return, now active individuals will also be able to increase the amount of oxygen to their lungs, organs and bloodstream—providing a boost that will enable them to sustain or restore energy.

When portability is required the typical delivery mode is via compressed oxygen in a pressure vessel. Typically, canisters are provided that contain 1-8 liters (when measured at standard temperature and pressure) of product that is compressed to between 20 and 150 atmospheres. The highly compressed gas is held in containers made of aluminum, steel, or other suitable material, and is often referred to as "canned oxygen." Unlike medical oxygen, which is delivered continuously or as a bolus triggered by inhalation, supplemental oxygen users typically actuate a valve that releases a 50 to 200 ml burst of oxygen, which is directed at the nose and/or mouth during inhalation. Five to 40 bursts per container are typically provided. Various benefits are attributed to the practice of breathing oxygen including, but not limited to: increased stamina, reduced fatigue, improved mental acuity and focus, improved complexion, improved general health, and reduced hangovers, jet lag, altitude sickness, headaches, general fatigue, and effects of airborne pollution.

As a result, "canned oxygen" or "recreational oxygen" is often used by athletes, people in cities with suspect air quality, active people, and others concerned about their general health. The use of this type of oxygen is rapidly increasing as cities become more polluted, stress levels increase, and people become more interested in health and performance issues.

In relation, many oxygen bars were established so people could take advantage of the beneficial effects of breathing pure oxygen for a fee. Many users claimed that they felt refreshed and had more energy after a session. The problem was is that it was not convenient for users since they had to sit at the bar and the general public could view the person with an oxygen cannula hooked to their nose for a prolonged period. With this as evidence it is easy to see that there is a need for a safe, convenient, inexpensive and novel reusable container form factor to deliver both water and oxygen to consumers for their daily use.

Efficacy of Oxygen ($O^2$)

At the molecular level, oxygen is energy. Ninety-percent (90%) of the human body's energy comes from oxygen and the other 10% comes from food and water. Oxygen is the most vital nutrient for cell reproduction and growth in the human body. The inhaling of pure oxygen, also referred as Oxygen Enriched Air (OEA) results in immediate relief from fatigue, jet lag, motion sickness, stress, altitude sickness, alcohol sickness and many more maladies. Furthermore, the lungs provide the primary control of our energy level and they extract oxygen from the air we breathe primary on the exhale. With supplemental oxygen use, the body will metabolize food more efficiently, generate more energy and create a healthier body.

Enhancement of exercise performance through the utilization of naturally derived supplements and hydration strategies provides a means by which athletes of varying abilities and levels may increase their proficiency and effectiveness. Preventative strategies ensure continued high-level performance, allowing the athlete to progress along the continuum of training, and can provide prohibitive insurance against decreased performance.

With oxygen, the body will metabolize food efficiently, generate more energy and create a healthier body. In essence, it is the "food" for our cells. If there is enough oxygen around our cells, then our organs and tissues have plenty of "food" and most likely will function properly. If our cells are not properly nourished, the message to our brain is "feed us". That is why you see athletes breathing oxygen at a sporting event because they know that oxygen increases their performance, endurance, and energy level. Athletes and athletics require a tremendous amount of oxygen to convert carbohydrates, sugars, fats, and proteins. However, oxygen is the "Fuel" required to oxidize all or any of these foods. Without the presence of oxygen, these foods would oxidize very poorly resulting in poor cellular reproduction and function, which would cause inadequate production of energy. Since oxygen is the main fuel required to metabolize your body's functions—why wouldn't people utilize what nature initially was trying to provide us.

The medical community comprehends that without adequate amounts of oxygen in our bodies, our cells become less efficient, inhibiting reproduction and growth, and eventually becoming sick cells. The greater the sick cells a person accumulates, the greater chance of that person becoming ill. A prime example of this is the device known as the Hyperbaric Chamber. Doctors utilize this pressurized oxygen device to treat many debilitating diseases. It quickly enables the human body to absorb oxygen, thus feeding the body's blood stream to fight the effects of disease. A modification of this device that is being used by athletes to fight disease and promote healing is the oxygen tent. Many athletes and active individuals have found the healing powers of oxygen use through this kind of device.

Some compelling facts about oxygen and the human body:

Everyday each human breathes oxygen 20,000 times on average.

The human brain, which makes up just 2% of the human body, requires 20% of the oxygen.

By mass, the oxygen molecule makes up 90% of the water molecule; the water molecule makes up 65-75% of the human body Cancer attacks every organ of the human body except the heart because of its constant supply of oxygen.

Blood is the liquid carrier of oxygen that fuels all of the bodies' functions; stimulating chemical reactions; and cleaning itself of waste and toxins.

Research has shown that a human's lung capacity decreases 5% for every decade of life.

Less than 200 years ago the Earth's atmosphere contained over 40% oxygen; today we breathe ~21%

Livable Environment

Oxygen gives the world life, and equally important, it is what nature continually provides to sustain life. Humans, animals, trees, and plants have always been genetically equipped and raised within an oxygen-based ecosystem. All humans are oxygen-based life forms. Unfortunately, most people live in an increasingly polluted environment which impacts the environmental air that we all breathe. That means that we are breathing a little bit of oxygen and a lot of toxins which causes detrimental health effects as each person ages. Much of our atmospheric oxygen is bound with pollution so it makes it that much harder to cleanse our internal bodily systems.

Anoxia literally means "a lack of oxygen" and it could be said that is the current problem facing the world. Studies have shown that each person is breathing in about a tablespoon of dirty particulate matter each day. Day after day, month after month, year after year its inundating a persons' system. Wherever a person lives or goes, their lungs are being bombarded and overloaded with dirty particulate matter seeping into their blood and cells. This impacts the amount of energy that your body can generate resulting in declining health. If you body does not have enough energy (oxygen) to function properly, then the bacteria, viruses, funguses, pathogens and disease will start to thrive. One could say that the ultimate cause of all disease is a lack of enough oxygen to clean out our inner fluid environments. The lack of oxygen allows the two major causes of all disease to overcome the human body: toxic build-ups, and the formation of various colonies of micro-organisms inside each person. The toxins poison us, and the organisms sap our inner cell energy by releasing more toxins. If our inner oxygen levels are not restored to work optimally the result is damage to a person's ongoing health.

When a person's body has less oxygen to carry out its bodily functions, then the fluids, cells, cell walls are probably not efficiently doing their job. The mitochondria inside the cells are the electrical powerhouses of the body. That means that the body needs a sufficient supply of oxygen for the mitochondria to efficiently burn food and to generate energy. If the mitochondria are sitting in the cell, and in dirty cellular fluid, then it cannot generate energy efficiently. The present invention described herein addresses the need to effectively flood the body with supplemental oxygen and water to provide the energy that every person on the planet needs to sustain bodily function equilibrium and health. The oxygen provides the energy, and the water provides the means by which the energy is carried throughout the body Efficiency of Nose Breathing Breathing nasally using the means of the inventive device is a very important design aspect of the invention. In relation, it incorporates an ingenious way to utilize this "correct" form factor for the inhalation method. It is a scientific fact that the lungs are the primary organs that control the body's energy level. They extract oxygen from the air we breathe primarily on the exhale. Because the nostrils are smaller than the mouth, air exhaled through the nose creates back pressure on the exhale—it slows the air escape, so the lungs have more time to extract oxygen from the inhaled air. It also imposes approximately 50 percent more resistance to the air stream in normal individuals than does mouth breathing, resulting in a 10-20 percent more oxygen intake. When a person has a proper oxygen-carbon dioxide exchange, the blood will maintain at a balanced PH. If carbon dioxide is lost too quickly, as in mouth breathing, oxygen absorption is decreased. Another fact is that mouth breathing also accelerates water loss, which increases possible dehydration. At rest, we rely on our noses for about 70 percent of our breathing. But when we start exercising, we use our mouths a lot more, relying on our noses for just 27 percent of airflow.

Additionally, breathing through our noses is a lot more efficient than through our mouths. When we breathe through our nose, oxygen is pulled into all five lobes of the lungs. The mouth only allows oxygen to be pulled into the two uppermost lobes. Oxygen in all five lobes helps increase blood flow and helps protect organs and muscles from damage. The simple fact is that when inhaled from the mouth—a large percentage of the oxygen will end up in the stomach. Since the human stomach is an inefficient mechanism for absorbing oxygen, the user is just wasting the benefits of the inhaled oxygen. This is why medical applications use a mask or inhalation tube for the nose.

Another benefit of our breathing configuration is that it promotes deep nasal breathing. This helps transport nitric oxide (NO)—a very potent lung and blood vessel dilator that resides in your nasal passages—to your lungs. And since it's located in the highest concentration in the back of your nose, deep breathing is also the best way to increase NO to help your lungs and blood vessels open up better and function more efficiently. The flow of air that happens when you breathe through your nose allows very rich sources of NO to be fuel injected in the system.

The Growth of New Age Beverages

Press reports continue to associate carbonated soft drinks with the expanding waistlines of Americans, especially children. Municipalities around the country have barred the beverages from schools and other community locations. With the advancements in scientific research, the general population is more aware of the importance of living a healthy lifestyle and thus behaviors have changed. Generally, people are becoming more knowledgeable about what it takes to be healthy. Health and wellness continue to shape consumer choice in the New Age non-carbonated beverage category, which was the fastest growing beverage product category. This category includes the following:

Energy Drinks/Infused Water

Fruit Juices and Drinks

Bottled/Canned Teas

Sports Drinks

Beverage Additives

Consumers today are spending more and more money on products that promote a healthy lifestyle. People's attitudes about healthy living have changed drastically over the past twenty years. Consumers are more knowledgeable about the benefits of living healthier, thus the many products that promote healthy living have seen record sales in recent years. With this in mind, consumers have been making the adoption to reusable water bottles for convenience and to address their environmental concerns regarding single use plastic water bottles. This has been the precursor to growing a $8 billion a year worldwide market. With the increase in consumers wanting products that promote a healthy lifestyle, it has brought about the advent of functional beverages and portable drink enhancers and other flavored additive tablets to add flavorings to ordinary water. The present invention addresses the need for a reusable water bottle that can mechanically attach and detach these kinds of portable accessory products, including oxygen, to enhance the consumer experience of having different user experiences at their disposal during leisure, physical activity, recovery from fatigue, and at their disposal during the use of a portable liquid container. Some products that could be used to attach to the portable liquid container includes liquid flavor enhancers, powder additives, dissolvable tablets, and a person's personal affects like keys, identification, towels, cosmetics, mobile devices, etc.

Another favorable trend for our invention is the increased participation and competitiveness in sports around the world. The effects of hydration and clean oxygen are extremely beneficial to athletes. When a participant is lacking the proper amount of water and oxygen, their performance suffers. In today's competitive sporting landscape, athletes are looking for anything that will boost their performance. This inventive product offers active individuals what no other product does—a reusable water bottle that uses an attachment mechanism to secure a oxygen module in one convenient configuration.

Consumer Trends

Consumers Desire for Healthier Lifestyles: People in this specific market niche hold an increased desire to live a healthy lifestyle. This group forged the way when the bottled water craze exploded into the marketplace and they will undoubtedly lead the way when the oxygen craze begins. This was genuinely evident when the "low carb" craze became mainstream. The health-conscious consumer carefully selects products that improve their mental and physical health. They are willing to pay a premium for healthy products. Although the many bottled water companies initially fulfilled the health-conscious consumer's need for clean, purified water, the shifting need for a reusable water bottle is still present. Furthermore, the need for readily available clean oxygen has not been met so our invention described herein is poised to fill this need.

Athletes: Athletes are continually faced with the limitations of their cardiovascular capacity when exerting themselves—this is regulated by how much oxygen our heart and lungs can deliver to our cells. When muscle cells spring into action, they must have energy to burn and the waste products of that metabolism removed. Athletes are forever seeking the extra edge to boost their performance to optimum levels. Athletes require tremendous amounts of oxygen to convert carbohydrates, sugars, fats, and proteins into heat and energy required for their high level of activity. This conversion process is known as oxidation. The body oxidizes (burns) carbohydrates, sugars, fats, and proteins to create energy. Oxygen is the fuel required to oxidize any and all of these foods. When an athlete lacks sufficient amounts of oxygen, he or she will quickly become fatigued, both mentally and physically. As a result of fatigue, lactic acid collects in the muscles causing soreness and pain. Receiving the proper amount of clean oxygen will promote up to 50% faster recovery from injury. Based on activity levels, athletes have an increased need for readily available oxygen. This need is most visibly demonstrated by higher-level football teams having large, cumbersome oxygen machines on the sidelines that the players utilize after long runs and extended periods on the playing field. Our invention described herein will allow any and every athlete to have easy access to the benefits of clean oxygen and the convenience of a reusable water bottle.

Citizens in Highly Polluted Area's: In recent years, numerous studies have surfaced about the staggering link between air pollution and disease. Research continues to show the affects air pollution has on the human body. People are suffering as a result of not getting the proper amount of clean oxygen in their bodies. Our inventive product described herein will enable a behavioral change with regards to the effects of the air that people breathe.

Basic Wellness Needs: It's simple . . . humans need clean oxygen. Today's breathable air contains only 21% oxygen and our invention enables a person to inhale over 4× that amount. Humans struggle from day to day with symptoms of fatigue, circulation problems, poor digestion, depression, memory loss, muscle aches and pains, headaches, hangovers, and poor concentration. All of these symptoms are directly related to oxygen deficiency. People have a need for a simple solution to curing these common ailments. Our invention will aid in overcoming these symptoms by having the much-needed clean oxygen readily available at any time.

Stressed People: In today's fast-paced society, many people are easily over-stressed. Stress can wear a person down both mentally and physically. People need a product that can aid in relieving stress in a healthy manor. Stress can be partially caused by the lack of oxygen in one's system. Clean oxygen can ease the tensions within the body by providing the cells with the proper amount of fuel to produce the energy to relax and calm it. Our invention will be conveniently available to curb and lessen the detrimental effects of everyday stress on one's health.

Fatigued People: With lifestyles today, fatigue is rarely avoidable, and often times occurs on a regular basis. In this sleep-deprived society one operates in today, it is extremely difficult for the human body to carry out its functions and perform activities at desired optimum levels. As a result, many workers have turned to caffeine to help them get through the day. Coffee and soda are not a healthy option and have adverse effects on one's health. The more clean oxygen a person takes in, the more energy that is created within the body. So instead of purchasing a fat laden, unhealthy $6.00 latte at Starbucks, a person can simply take a few sips of water and rejuvenating breathes of healthy oxygen to feel naturally stimulated.

People Traveling to Higher Altitudes: When people travel to high altitude it is common to notice a faster breathing rate, shortness of breath upon exertion, broken sleep and acute fatigue. These changes are a normal response to the decreased availability of oxygen and the change of pressure in the atmosphere. To get all the oxygen you need you will find you have to breathe faster, but even with a faster breathing rate it is difficult to get adequate amount of oxygen for mental acuity and for your muscles. This invention is the answer to help people alleviate these symptoms in these high-altitude areas.

Smokers: The chemicals in cigarette and cigar smoke are known to inhibit the use of oxygen and constrict blood cells, which inhibits the body's ability to transport oxygen throughout the body. There is no better option than to quit, but oxygen use could help relieve some of the effects of this bad habit.

Drinkers: The consumption of alcohol cuts off the supply of oxygen to the brain and damages the liver by constricting blood vessels and reduces the delivery of oxygen to the body's liver cells. If you have ever experienced alcohol sickness or an alcohol "hangover", it is clear that people will gladly pay for relief of their symptoms.

Workers & Students: New studies show that the brain is boosted by the chemical synthesis of glucose and oxygen— this invention provides a mechanism to enhance this. The more oxygen and glucose present—an increase in memory, attention span and learning ability was seen in all age groups. An improvement in creativity and verbal fluency was also noticed.

Other features and advantages of the invention will become apparent from the following description of the invention and its accompanying drawings.

DETAILED DESCRIPTION OF THE INVENTION

Figure 1:
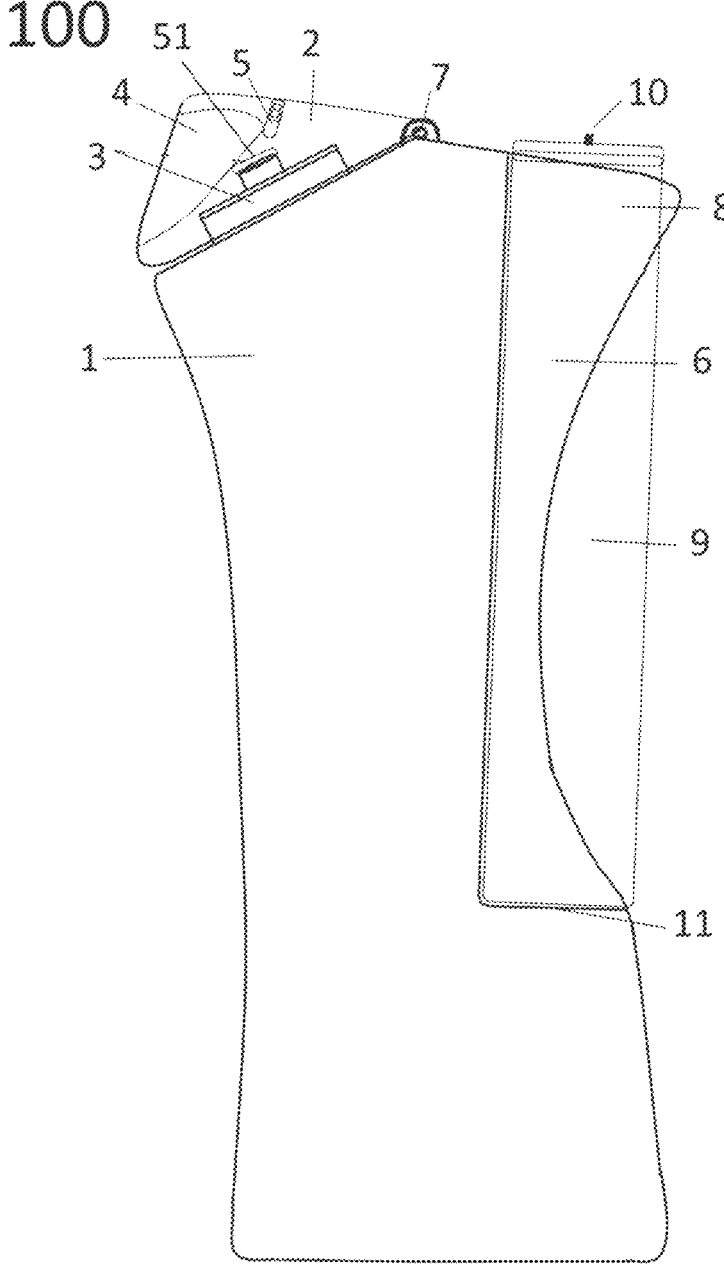
FIG. 1 shows the side view of an embodiment of the portable liquid container with the gas canister with a securing canister body cavity that allows a gas canister to be attached or detached when desired, with the dual-purpose lid cover over the liquid dispensing cap.

Referring to FIG. 1 outlines a portable liquid container 1 shown as 100 having a securing canister body cavity 6 with circular oriented appendages 8 and cavity floor 11 to attach a gas canister 9 in place. The portable liquid container 1 incorporates a dual-purpose lid cover 2 which incorporates a valve assembly 5 and nose cavity mask 4 that secures over the liquid dispensing cap 3 and liquid dispensing valve 51 which can be pivoted or rotated using a swivel hinge 7 to position and align over the securing canister body cavity 6 which holds a gas canister 9 with a canister dispensing nozzle 10 that is activated when pushed down to release a gas. The gas canister 9 can be attached and detached from the securing canister body cavity 6 of the portable liquid container 1.

Figure 2:
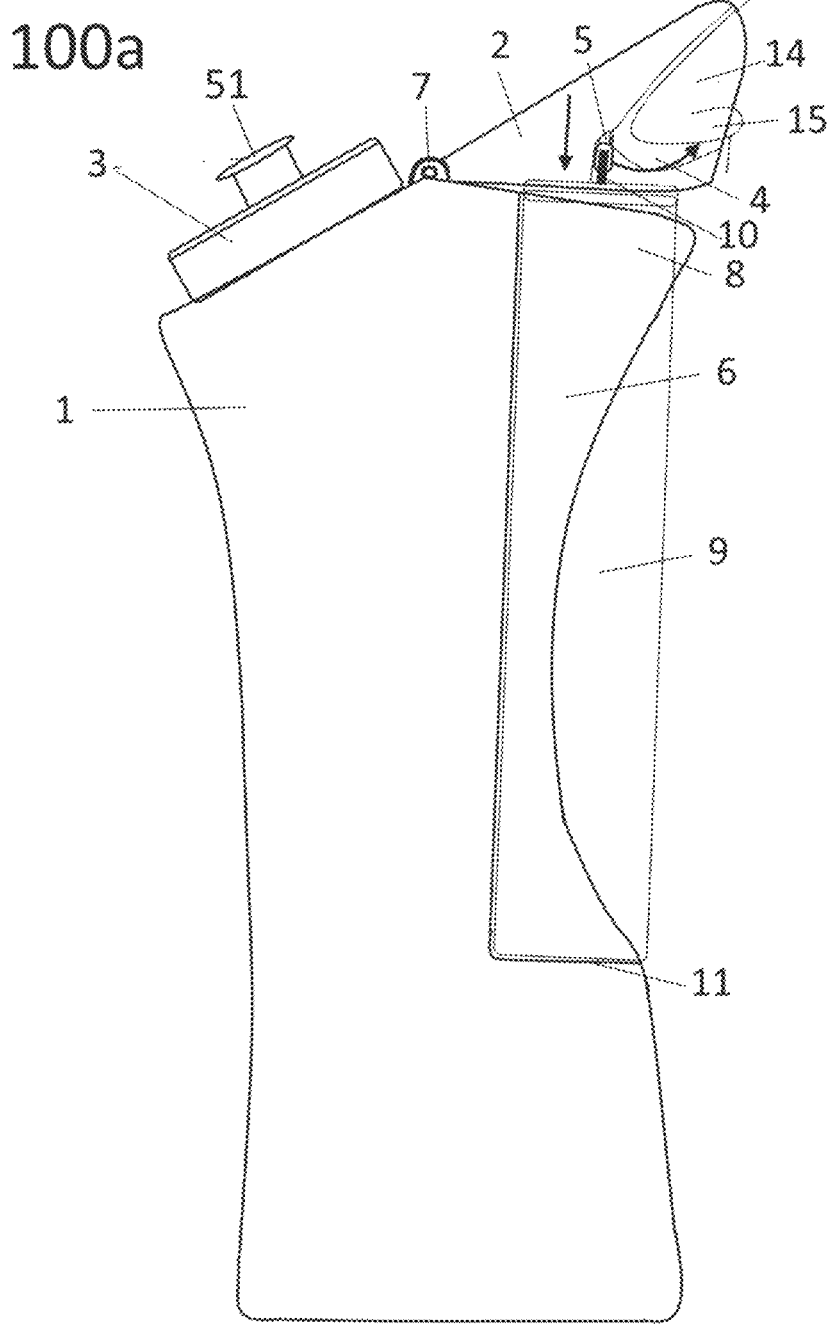
FIG. 2 shows the side view of an embodiment of the portable liquid container with the gas canister affixed in the securing canister body cavity with the dual-purpose lid cover in position over the gas canister to dispense a gas into a person's nose.

Referring to FIG. 2, outlines a portable liquid container 1 shown generally as 100*a* with a gas canister 9 with dispensing nozzle 10 attached in the securing body cavity 6 with circular oriented appendages 8 and cavity floor 11. The portable liquid container 1 incorporates a dual-purpose lid cover 2 that fits over the liquid dispensing cap 3 and liquid dispensing valve 51 which can be pivoted or rotated using a swivel hinge 7 to position and interface the valve assembly 5 of the gas canister 9 with canister dispensing nozzle 10. In this position the user has comfortable access to the nose cavity 4 and the valve assembly 5 is aligned with the canister dispensing nozzle 10. When the dual-purpose lid cover 2 is depressed and the valve assembly exerts downward force onto the canister dispensing nozzle 10 it releases a gas and allows it to flow into the nose cavity mask 4 into a person's nose 14 and inhaled into the nostrils 15. Any appropriate valve structure will work as is known in the art.

Figure 3:
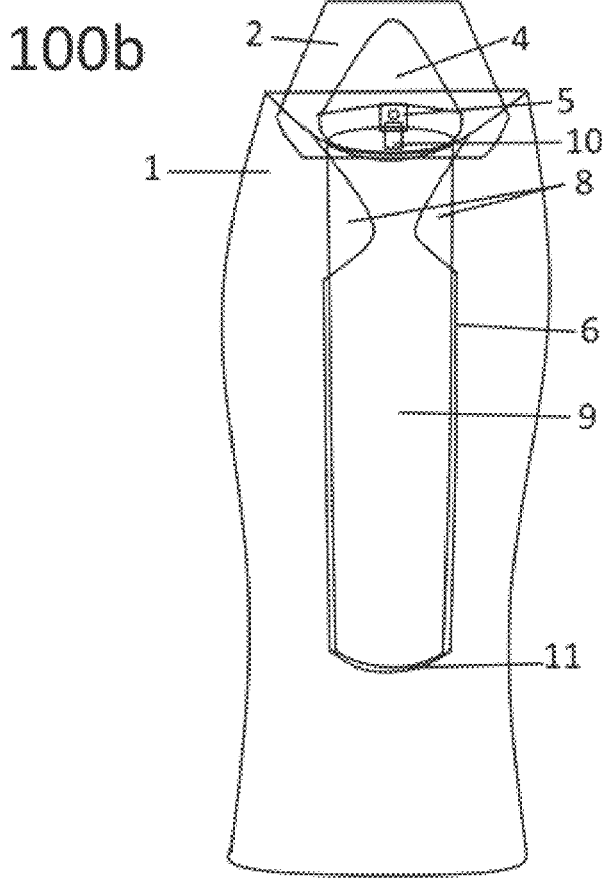
FIG. 3 shows the posterior view of an embodiment of the portable liquid container with the gas canister affixed in the bottle cavity with the dual-purpose lid cover in position over the gas canister.

Referring to FIG. 3 outlines a portable liquid container 1 shown as 100*b* from a side perspective from the gas canister 9 which is affixed inside the securing body cavity 6 with circular oriented appendages 8 and cavity floor 11. The portable liquid container 1 incorporates a dual-purpose lid cover 2 which is rotated to position the valve assembly 5 of the gas canister 9 with canister dispensing nozzle 10. In this position the user has comfortable access to the nose cavity 4 and the valve assembly 5 is aligned with the canister dispensing nozzle 10. When the dual-purpose lid cover 2 is depressed and the valve assembly exerts downward force onto the canister dispensing nozzle 10 it releases a gas and allows it to flow into the nose cavity 4 into a person's nose 14 and inhaled into the nostrils 15 (not shown). Any appropriate valve structure will work as is known in the art.

Figure 4:
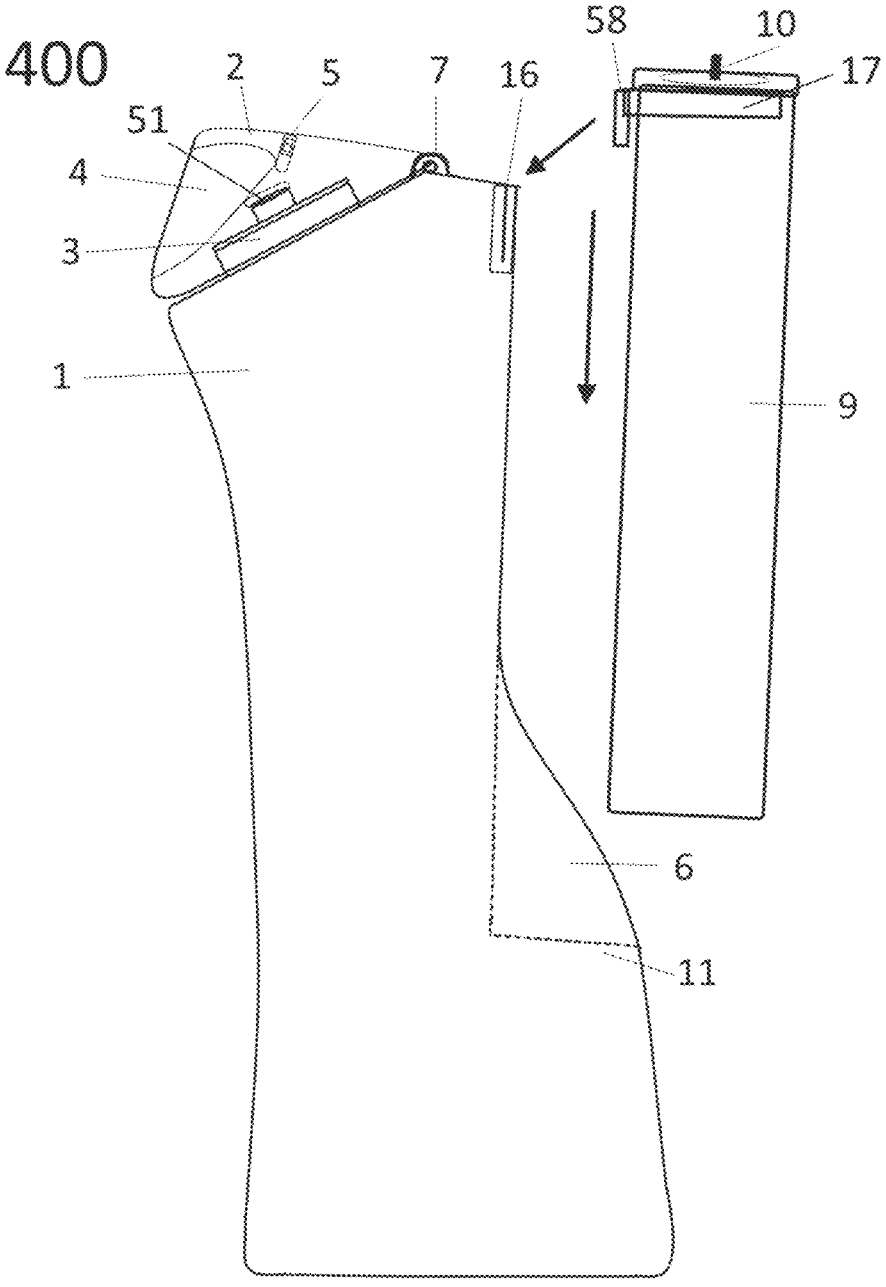
FIG. 4 shows the side view of an embodiment of the portable liquid container with an embodiment using an attachment housing incorporated into the portable liquid container body and with the gas canister attached to an attachment ring to affix the gas canister to portable liquid container.

Referring to FIG. 4 outlines a portable liquid container 1 shown as 400 with dual purpose lid cover 2 with nose cavity 4 and valve assembly 5 positioned over liquid dispensing cap 3 and liquid dispensing valve 51. Portable liquid container 1 incorporates an attachment housing 16 built into body to accommodate an attachment pin 58 with attachment ring 17 that is affixed to the gas canister 9. All other explanations are the same as all other figures presented.

Figure 5:
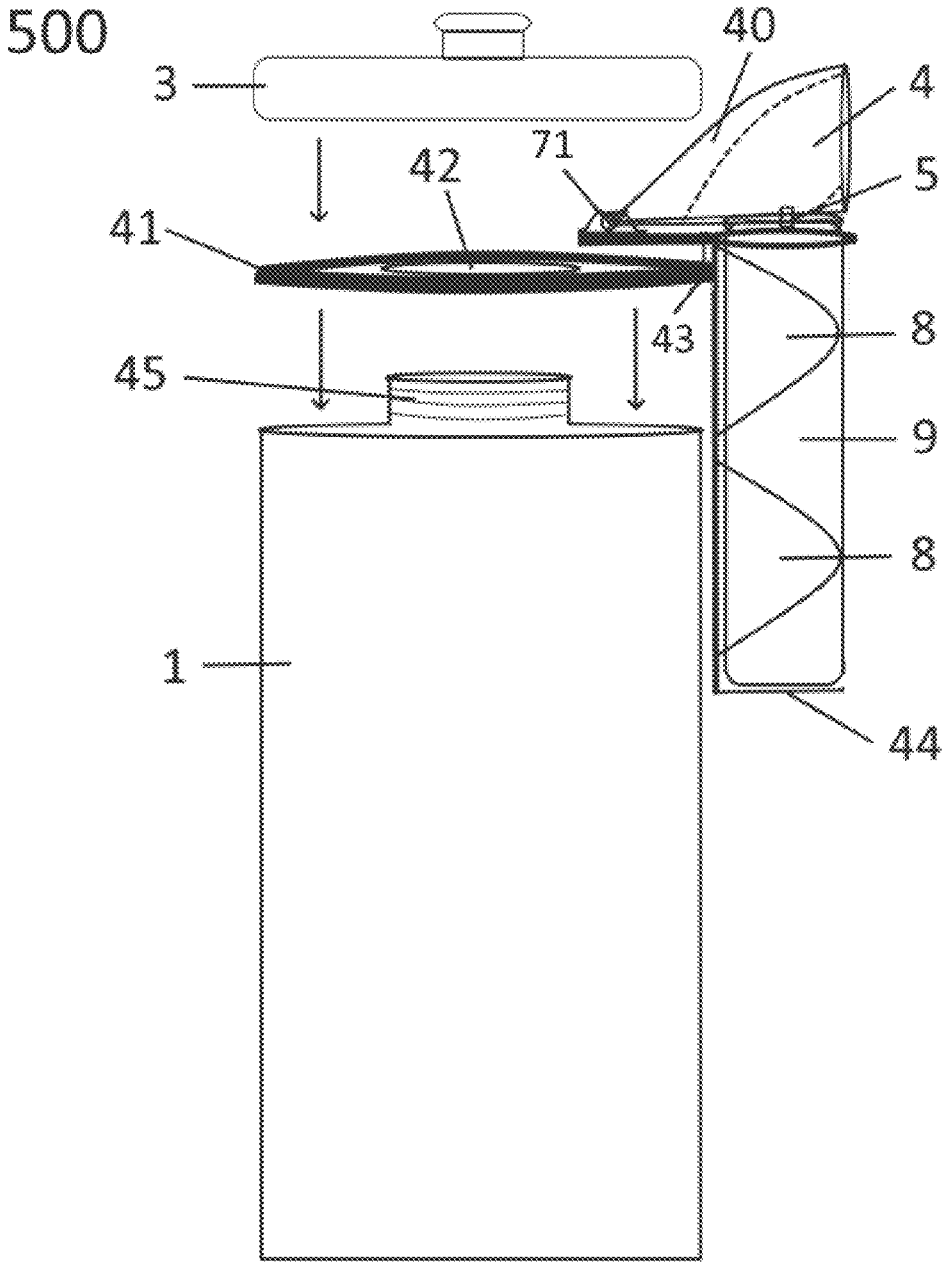
FIG. 5 shows an embodiment of the portable liquid container showing portable liquid container neck attached to gas canister module using bottle opening base to attach gas canister with nose inhalation mask in position for inhalation.

Referring to FIG. 5 outlines a portable liquid container 1 shown as 500 with a bottle opening base 41 with a container neck opening 42 that is placed over the portable liquid container neck 45 attached to adjustment mechanism 43 to allow for different size height adjustments to accommodate different size bottle cap heights in relation to the top of portable liquid container 1. Attached to gas canister module 48 is a nose inhalation mask 40 which incorporates a nose cavity 4 attached to a one way hinge 71 which allow a person to insert nose 14 and inhale through the nostrils 15 when the nose inhalation mask 40 is depressed to engage the valve assembly 5 to release gas through the canister dispensing nozzle on gas canister 9 which is being held in place by circular oriented appendages 8 and canister base 44.

Figure 6:
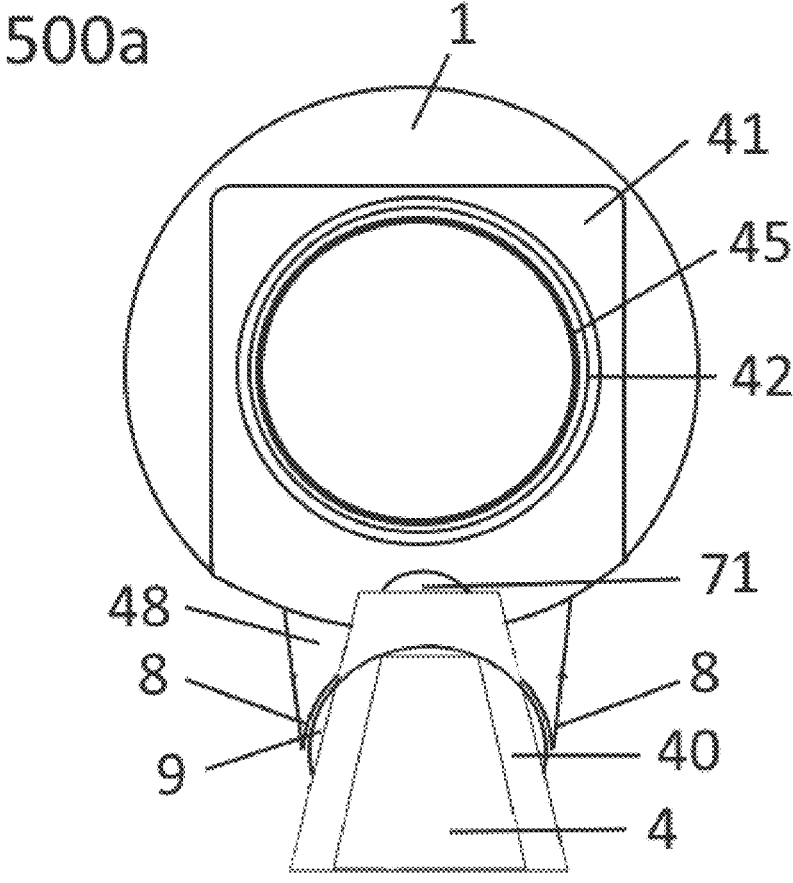
FIG. 6 shows the top view of FIG. 5 of the portable liquid container with portable liquid container neck attached to gas canister module using bottle opening base with nose inhalation mask in position for inhalation.

Referring to FIG. 6 outlines a top view of FIG. 5 with portable liquid container 1 shown as 500*a* without liquid dispensing cap showing portable liquid container opening base 41 with a container neck opening 42 to show how it is placed over portable liquid container 1 and portable liquid container neck 45 attached to gas canister module 48 that includes one way hinge 71 and circular oriented appendages 8 to hold gas canister 9 and is attached to nose inhalation mask 40 with nose cavity 4 that allows a person to insert nose and inhale gas through nostrils (not shown). All other explanations are the same as all other figures presented.

Figure 7:
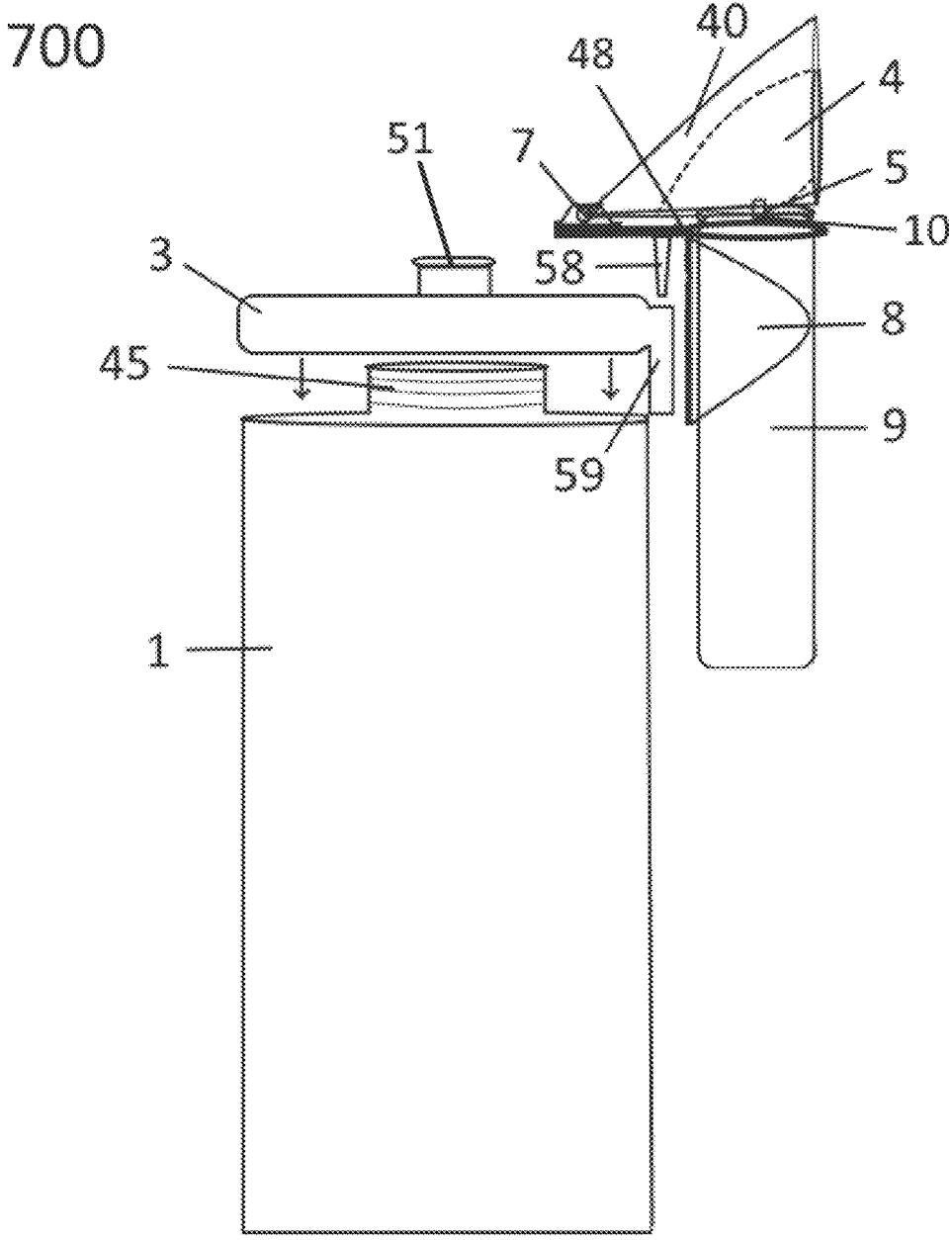
FIG. 7 shows an embodiment of the invention with portable liquid container showing an attachment mechanism clip/buckle incorporated into the liquid dispensing cap with a portable gas canister module with an attachment pin with a gas nose inhalation mask that affixes and detaches into two separate units.

Referring to FIG. 7 outlines a portable liquid container 1 shown as 700 with a liquid dispensing cap 3 with liquid dispensing valve 51 detached from portable liquid container and that attaches to portable liquid container neck 45. Liquid dispensing cap 3 is incorporated with attachment mechanism clip/buckle 59 which accepts the attachment pin 58 on gas canister module 48 to lock and release from portable liquid container 1 which includes swivel hinge 7 that is attached to nose inhalation mask 40 with nose cavity 4 that allows a person to insert nose and inhale gas through nostrils (not shown) which is activated when valve assembly 5 activates canister dispensing nozzle 10 while circular oriented appendages 8 holds gas canister 9. All other explanations are the same as all other figures presented.

Figure 8:
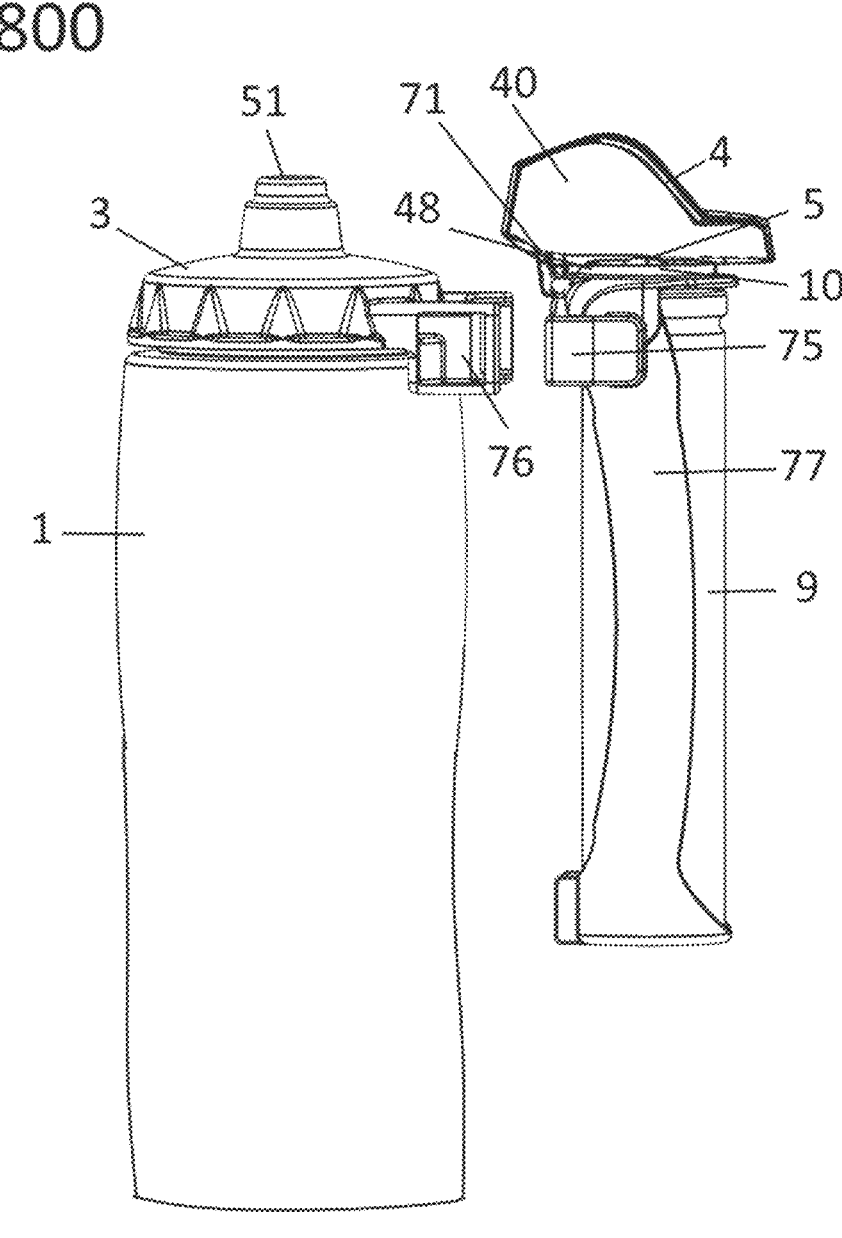
FIG. 8 shows an embodiment of the invention with a portable liquid container showing an attachment mechanism horizontally extending from the liquid container cap with detached gas canister module with attachment clips with nose inhalation mask in position over gas canister.

Referring to FIG. 8 outlines a portable liquid container 1 shown as 800 with embodiment of liquid dispensing cap 3 with liquid dispensing valve 51 with female attachment mechanisms 76 that extend horizontally to accommodate male attachment clips 75 on gas canister module 48 with one way hinge 71 attached to nose inhalation mask 40 with nose cavity 4 situating valve assembly 5 over gas canister 9 and canister dispensing nozzle 10 that allows a person to insert nose (not shown) and on depression inhale gas through nostrils (not shown) while canister side holding apparatus 77 holds gas canister 9. All other explanations are the same as all other figures.

Figure 9:
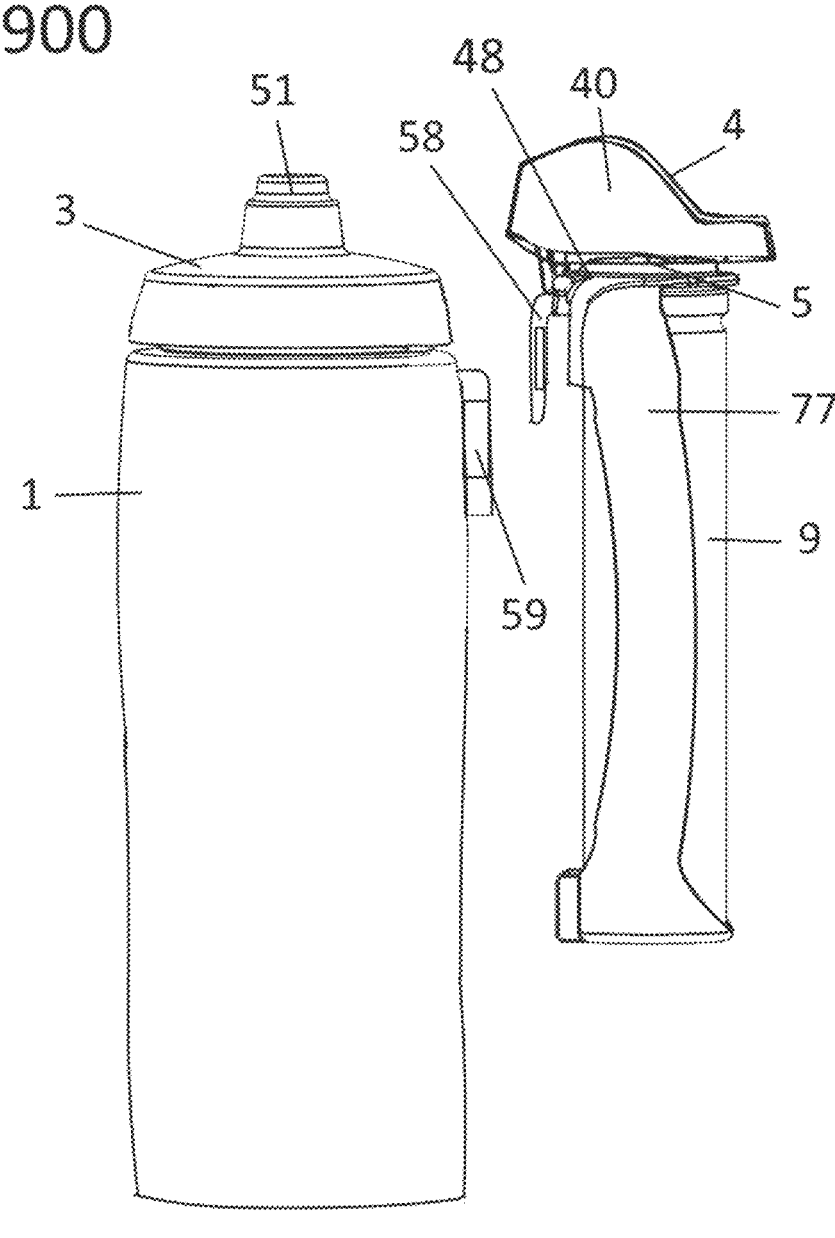
FIG. 9 shows an embodiment of the invention of portable liquid container with attachment mechanism integrated into portable liquid container body for attaching oxygen container module with nose inhalation mask or another portable container.

Referring to FIG. 9 outlines a portable liquid container 1 shown as 900 with embodiment with attachment mechanism clip/buckle 59 that is incorporated into the body of portable liquid container 1 for securing attachment pin 58 of gas canister module 48 with one way hinge 71 attached to nose inhalation mask 40 with nose cavity 4 situating valve assembly 5 over gas canister 9 and canister dispensing nozzle 10 that allows a person to insert nose (not shown) and on depression inhale gas through nostrils (not shown) while canister side holding apparatus 77 holds gas canister 9. All other elements are the same as all other figures.

Figure 10:
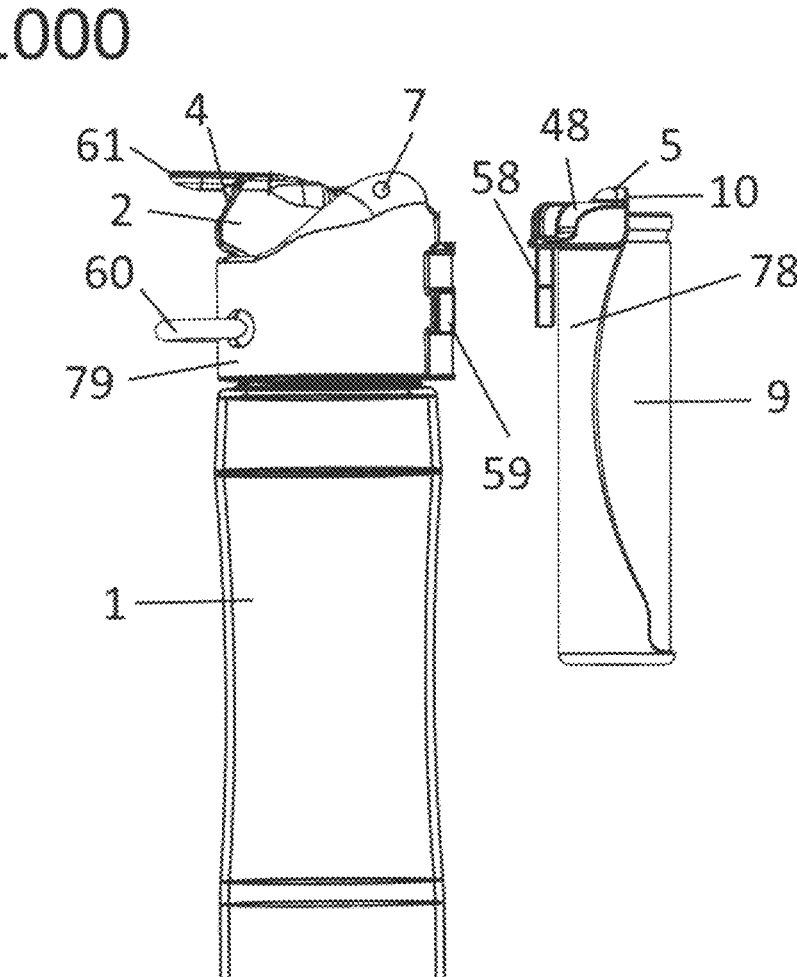
FIG. 10 shows an embodiment of the invention of portable liquid container with dual purpose lid cover integrated into liquid container cap and nose inhalation mask covering swivel liquid dispensing valve (not shown) with gas canister module with gas canister detached.

Referring to FIG. 10 outlines another embodiment of the invention shown as 1000 with portable liquid container 1 with dual purpose lid cover 2 with nose cavity 4 with integrated depression tab 61 and valve assembly 5 attached to swivel hinge 7 integrated into liquid dispensing cap 79 with clip hook 60 while covering swivel liquid dispensing valve (not shown) showing detached gas container module 48 with gas canister 9 situated in canister enclosure 78 showing canister dispensing nozzle 10 with male attachment pin 58 detached from female attachment mechanism clip/buckle 59 on liquid dispensing cap 79. All other explanations are the same as all other figures.

Figure 11:
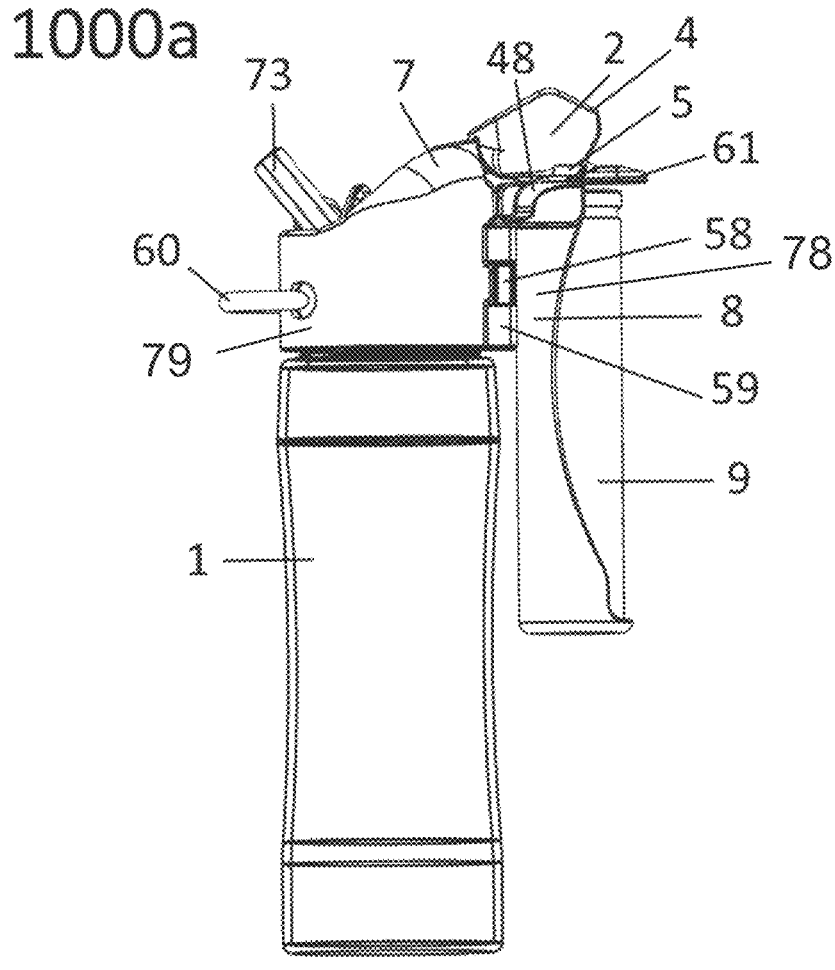
FIG. 11 shows an embodiment of the invention with portable liquid container with dual purpose lid cover swung into the nose inhalation position over the attached gas canister module that allows for the opening of the swivel liquid dispensing valve to be accessed.

Referring to FIG. 11 outlines a portable liquid container 1 shown as 1000*a* with oxygen container module 48 attached using attachment mechanism clip/buckle 59 and attachment pin 58 attached to liquid dispensing cap 79 with clip hook 60 using dual purpose lid cover 2 positioned over oxygen container module 48 using swivel hinge 7 to engage valve assembly 5 over canister dispensing nozzle 10 to enable the activation of the dispensing of a gas while pressing the depression tab 61 that allows a person to insert nose (not shown) and on depression inhale gas through nostrils (not shown) with canister enclosure 78 holding gas canister 9. Notice that in this position it enables the ability to access the swivel liquid dispensing valve 73 to drink. All other explanations are the same as all other figures.

Figure 12:
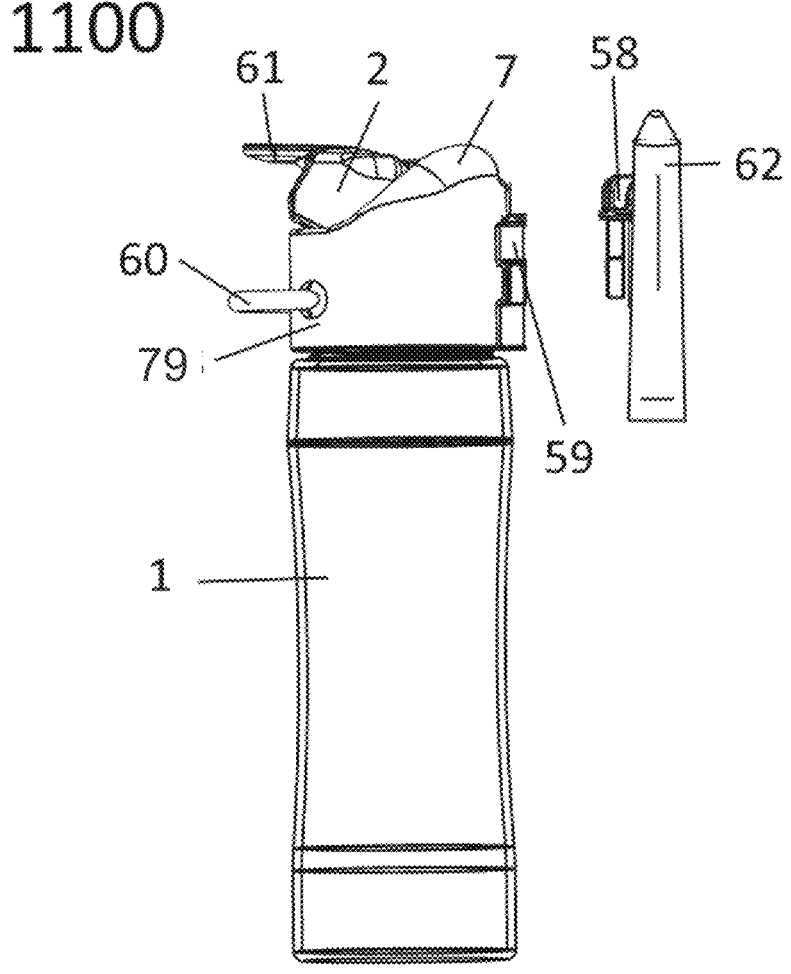
FIG. 12 shows an embodiment of the invention with portable liquid container with dual purpose lid cover covering swivel liquid dispensing valve with detached accessory container with attachment pin.

Referring to FIG. 12 outlines a portable liquid container 1 shown as 1100 with accessory container 62 with attachment pin 58 depicting it as being detached from attachment mechanism clip/buckle 59 incorporated into liquid dispensing cap 79 with clip hook 60. The dual purpose lid cover 2 is positioned over swivel liquid dispensing valve (not shown) using swivel hinge 7 to affix into liquid dispensing cap 79. All other explanations are the same as all other figures.

Figure 13:
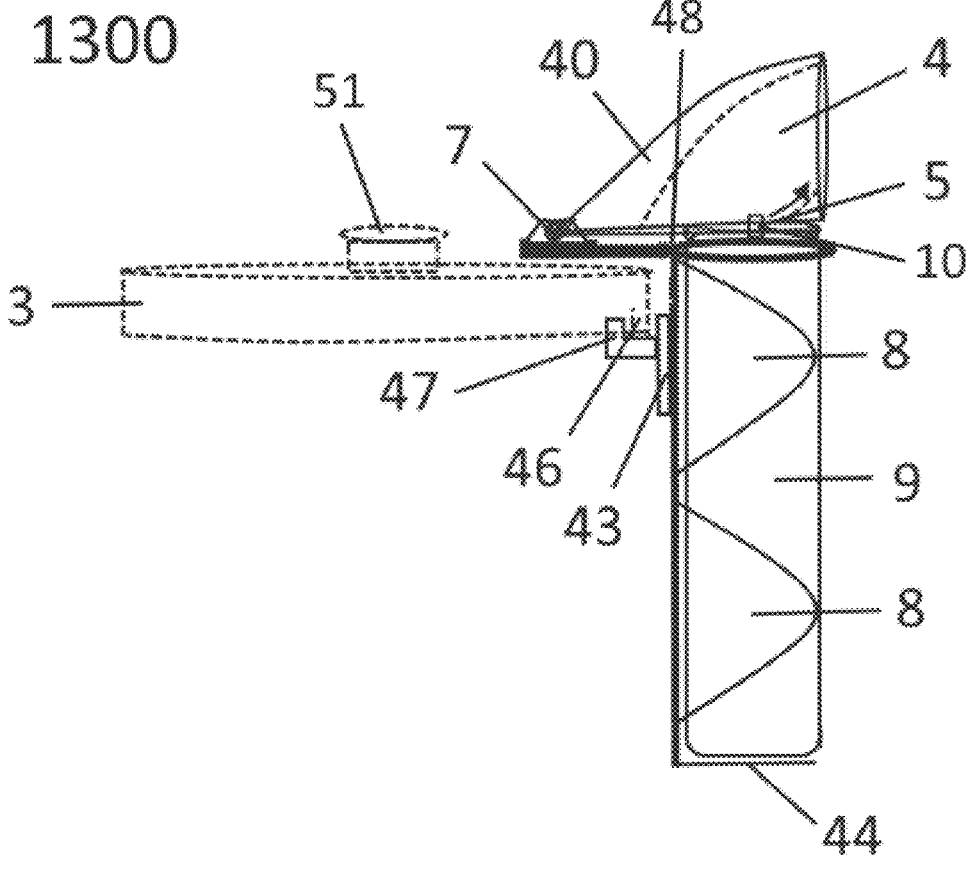
FIG. 13 shows another embodiment of the invention showing portable liquid container cap and cap edge being held by cap edge grip with adjustment mechanism that allows the apparatus to attach gas canister module to portable liquid container.

Referring to FIG. 13 outlines another embodiment of the portable liquid container 1 shown as 1300 that shows a liquid dispensing cap 3 with liquid dispensing valve 51 being affixed and held under the cap edge 46 by cap edge grip 47 which is attached to adjustment mechanism 43 to allow for different size height adjustments to accommodate different size bottle caps. Attached is a nose inhalation mask 40 with nose cavity 4 attached to a swivel hinge 7 to gas canister module 48 that allows a person to insert nose (not shown) and inhale through the nostrils (not shown) when the nose inhalation mask 40 is depressed to engage the valve assembly 5 to release gas into the nose cavity 4 from canister 9 and canister dispensing nozzle 10 that is being held in place by circular oriented appendages 8 and held up by canister base 44.

Figure 14:
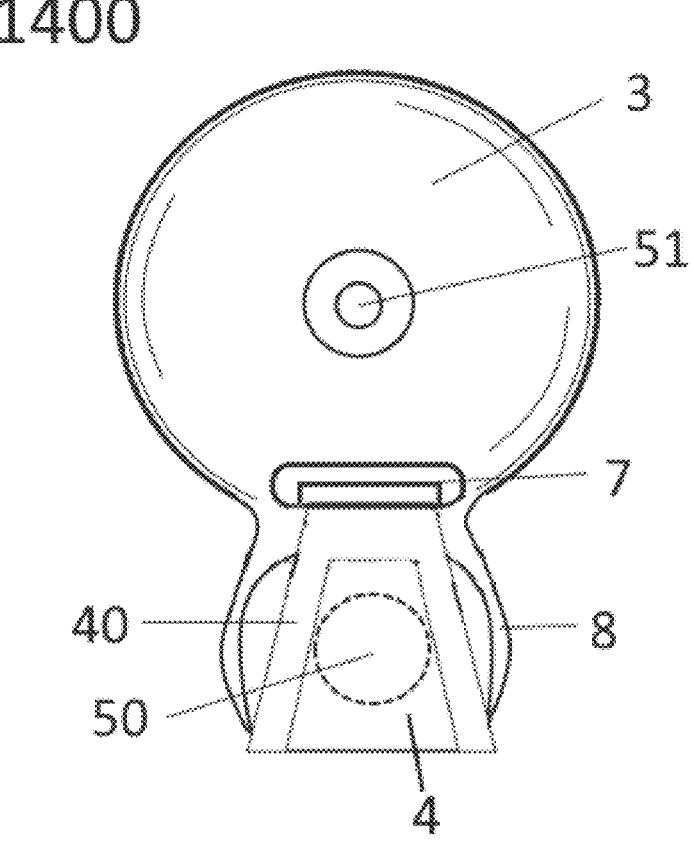
FIG. 14 shows a top view of another embodiment of the invention showing a portable liquid container cap that incorporates canister holding appendages and the dual-purpose lid and inhalation mask as one unit so it can be used to replace existing liquid container cap on portable liquid containers.

Referring to FIG. 14 outlines another embodiment of the invention shown as 2100 from an overhead perspective showing the liquid dispensing cap 3 and the liquid dispensing valve 51 and dual-purpose lid cover 2 in the nose inhalation mask 40 position with nose cavity 4 attached to swivel hinge 7 showing liquid dispensing valve indentation 50 and circular oriented appendages 8 as one unit built into the liquid dispensing cap 3 that can be used to replace any existing liquid dispensing cap that fits on a portable liquid container 1.

Figure 15:
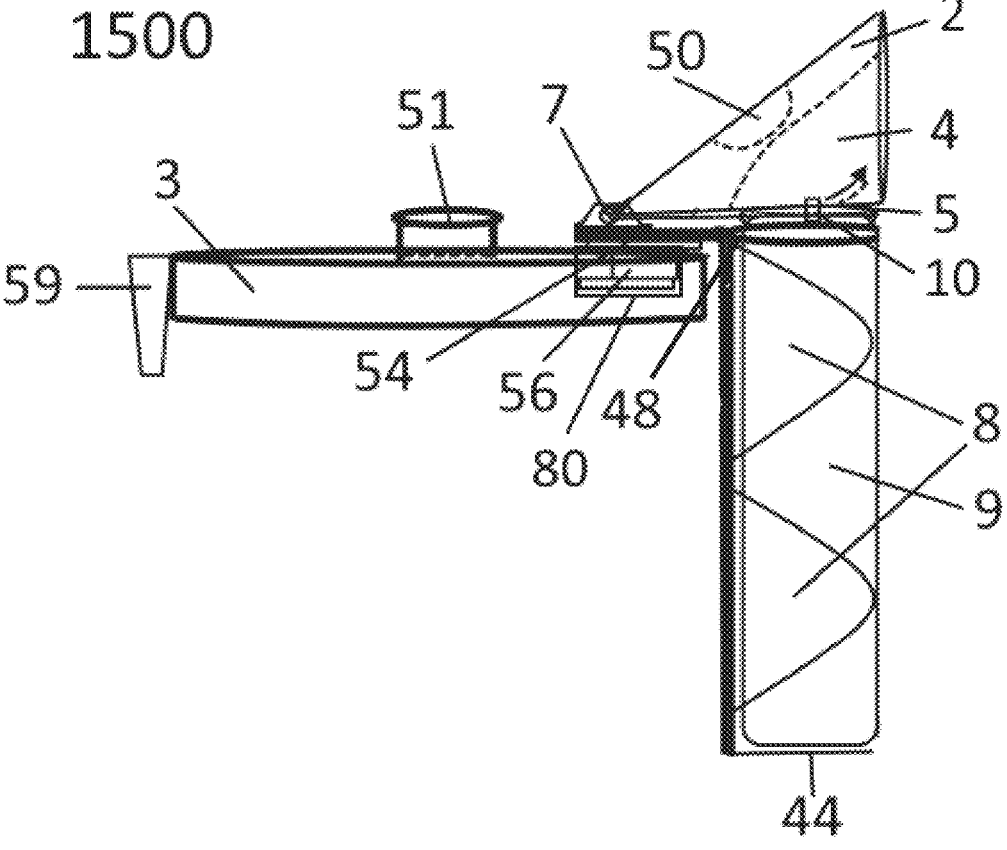
FIG. 15 shows a side view of another embodiment of the invention that shows gas canister module with slide clip affixed to liquid dispensing cap with cap attachment housing to affix and detach the canister module with nose inhalation mask over gas canister.

Referring to FIG. 15 outlines another embodiment of the invention shown as 1500 from a side perspective showing liquid dispensing cap 3 with liquid dispensing valve 51 incorporating cap attachment housing 56 with an attachment mechanism clip/buckle 59 incorporated to affix other accessories that have an attachment pin 58 (not shown). The gas canister module 48 includes a slide clip 80 incorporates a swivel hinge 7 with an affixed dual purpose lid cover 2 with nose cavity 4 and liquid dispensing valve indentation 50 that allows a person to insert nose (not shown) and inhale through the nostrils (not shown) when the nose inhalation mask 40 is depressed to engage the valve assembly 5 to release gas into the nose cavity 4 from canister 9 and canister dispensing nozzle 10 that is being held in place by circular oriented appendages 8 and held up by canister base 44. It allows the gas canister module 48 to be affixed and released for use with a portable liquid container 1. All other explanations are the same as all other figures.

Figure 16:
FIG. 16 shows the top view of another embodiment of the invention using a dual C-clamps to affix to the portable liquid container and the other to affix to a gas canister or accessory container.
Figure 16:
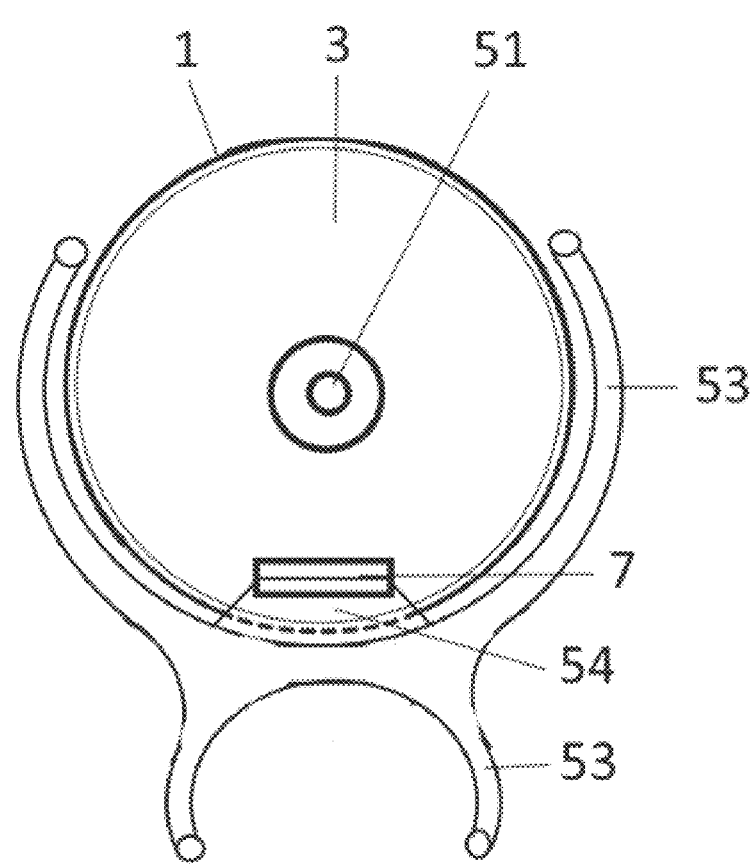

Referring to FIG. 16 outlines another embodiment of the invention shown as 1600 from the overhead perspective that incorporates a tension C-clamp 53 design that allows the apparatus to be affixed to a liquid dispensing cap 3 with liquid dispensing valve 51 on portable liquid container 1 using a base plate 54 and swivel hinge 7 that rests upon liquid dispensing cap 3 to position dual purpose lid cover (not shown) to affix a canister to another tension C-clamp 53.

Figure 17:
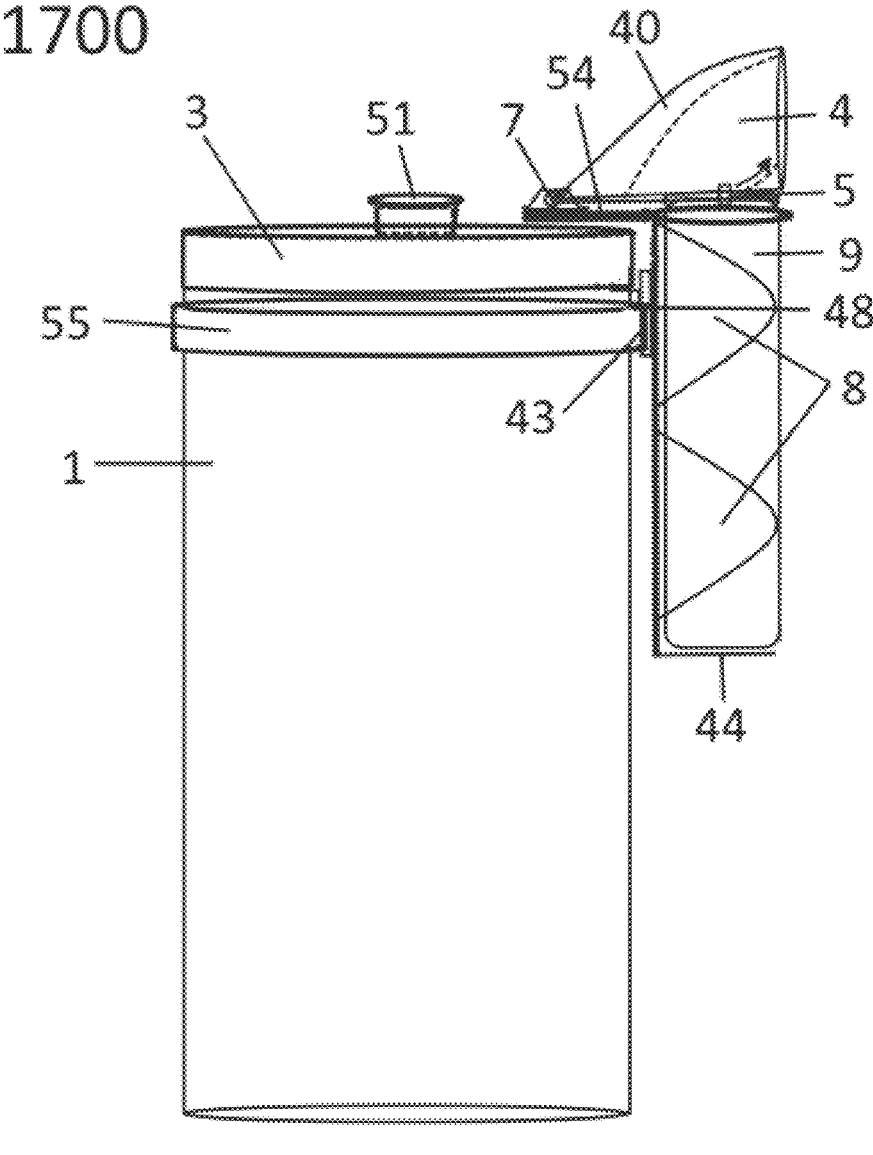
FIG. 17 shows the side view of another embodiment of the invention using an adjustable attachment strap affixed to a strap buckle that was incorporated into gas canister module with nose inhalation mask to affix portable liquid container.

Referring to FIG. 17 outlines another embodiment of the invention shown as 1700 from the side perspective that incorporates an adjustable attachment strap 55 that fits though strap buckle 43 which is affixed to the gas canister module 48 and to portable liquid container 1 or the area around the liquid dispensing cap 3. All other explanations are the same as all other figures.

Figure 18:
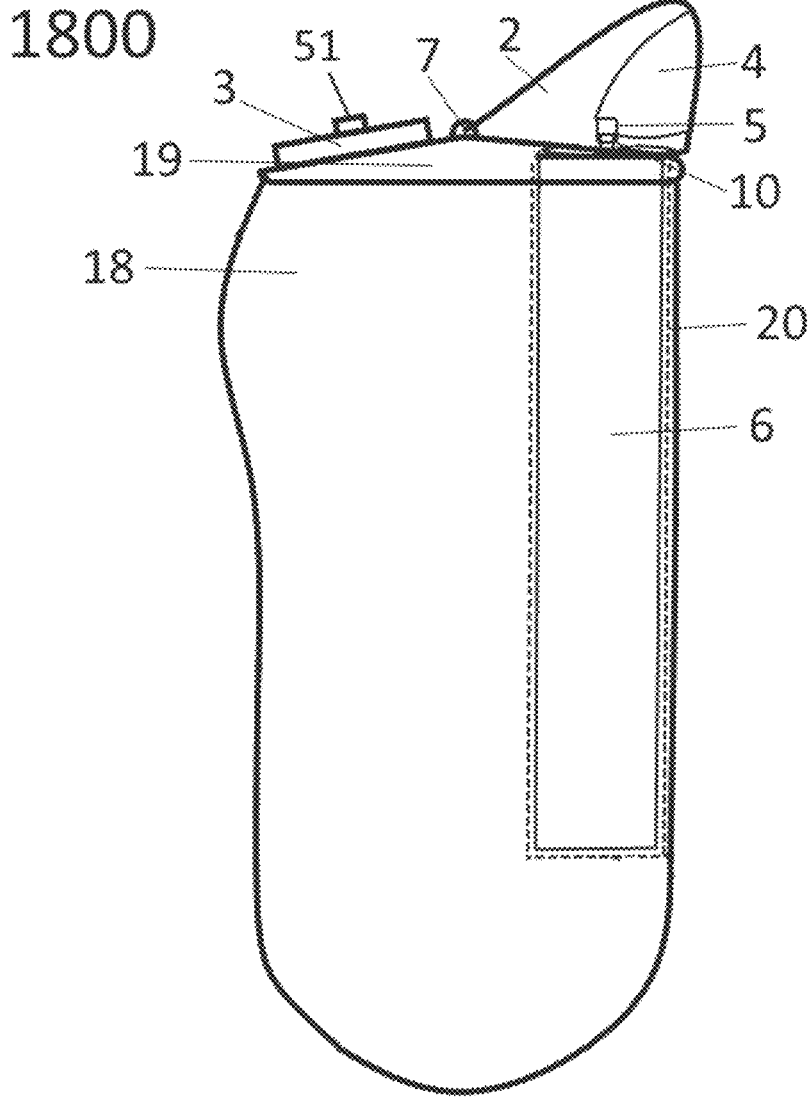
FIG. 18 shows another embodiment of the invention as a flexible liquid bladder with a compartment to hold a gas canister with dual-purpose lid cover as described herein for the separate dispensing of a liquid and a gas on demand.

Referring to FIG. 18 outlines a flexible reservoir container 18 shown as 1800 that includes a flexible body cavity 20 to house a gas canister 9 and incorporates a top fitting 19 that includes liquid dispensing cap 3 with liquid dispensing valve 51 utilize a dual-purpose lid cover 2 with swivel hinge 7 with nose cavity 4 and liquid dispensing valve indentation 50 that allows a person to insert nose (not shown) and inhale through the nostrils (not shown) when the nose inhalation mask 40 is depressed to engage the valve assembly 5 to release gas into the nose cavity 4 from canister 9 and canister dispensing nozzle 10. In this embodiment the flexible reservoir container can be made of any flexible material such as polyethylene, neoprene, silicone, etc., and inner bladder material can be impregnated with anti-fowling and anti-bacterial compounds to protect from mold and bacteria from populating inside the flexible reservoir container.

Figure 19:
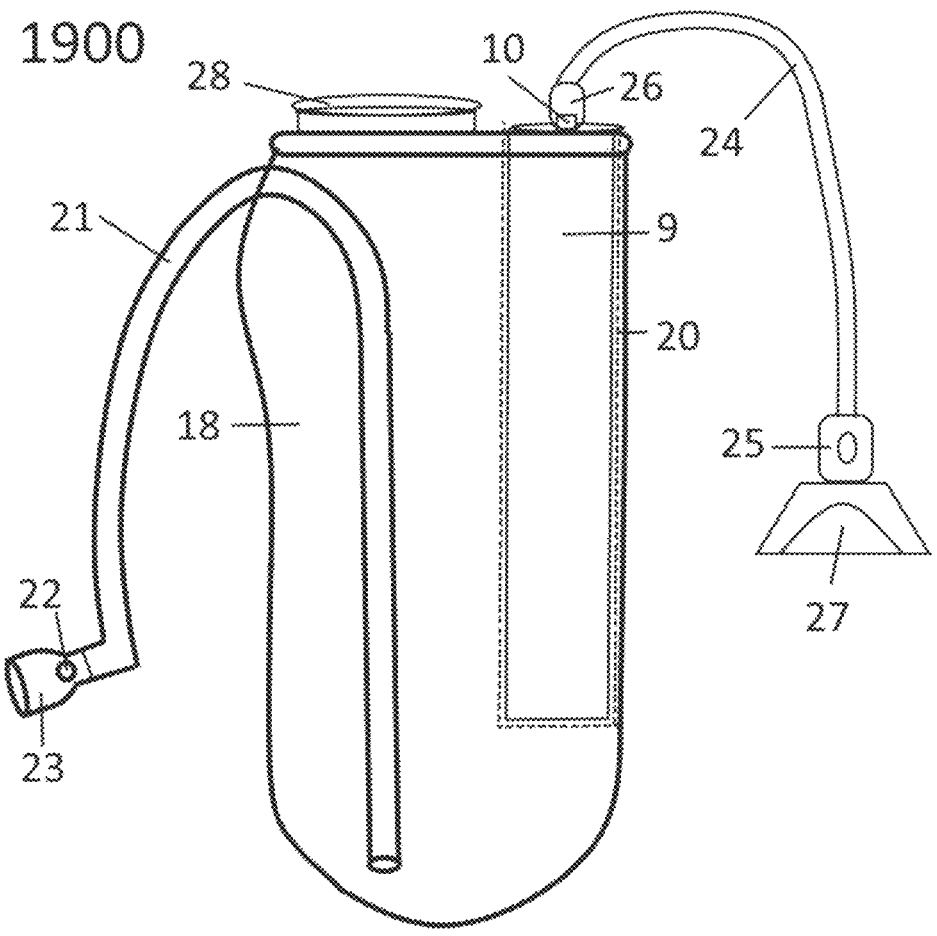
FIG. 19 shows another embodiment of the invention as a flexible liquid bladder with a compartment to hold a gas canister using user actuated dispensing supply lines for the separate dispensing of a liquid and a gas on demand.

Referring to FIG. 19 outlines a flexible liquid reservoir container 18 shown as 1900 that includes a flexible body cavity 20 to house a gas canister 9. In this embodiment it includes a liquid opening and closure cap 28 and a water delivery line 21 connected to the liquid side of the flexible reservoir bottle 18 to allow the dispensing of liquid on demand by actuating a release valve 22 which flows to a delivery mouthpiece 23. The gas canister dispensing nozzle 10 is connected by a pressure fitting 26 that opens the flow of gas while pressurizing the oxygen delivery line 24 to allow gas delivery by regulating a push button gas delivery regulator 25 which controls the on-demand flow of gas delivery to a flexible nose mask 27. The delivery line can be attached to other nose delivery-oriented form factors such as a nasal cannula to easily attach to the inside of the nostrils.

Figure 20:
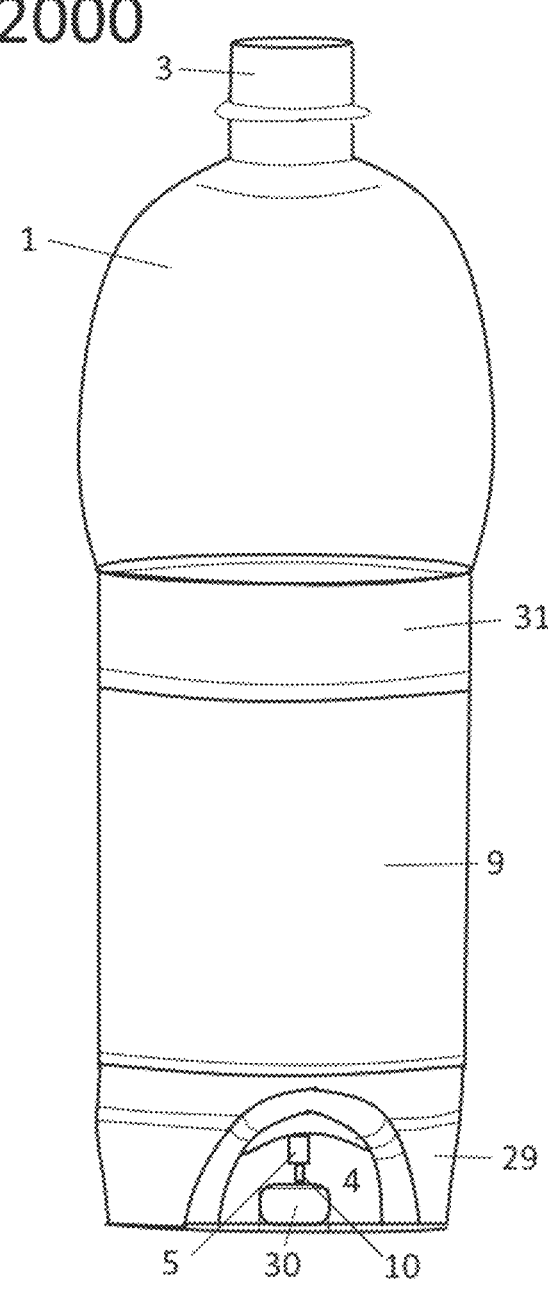
FIG. 20 shows another embodiment of the invention with a liquid container that attaches with a connection ring to the lower gas canister with inhalation nose mask adapter affixed to the ventral surface of the lower gas storage canister which also acts as the bottom surface so as to stand the invention upright.

Referring to FIG. 20 outlines a portable liquid container 1 shown as 2000 that affixes to a connector ring 31 that is affixed to the gas canister 9 bottom which is in an inverted position making the canister dispensing nozzle 10 face downward to interact with valve assembly of the inhalation nose mask adapter 29 and the valve assembly 5 of the gas canister which is activated by the depression of the actuator button 30. In this configuration the user can choose to position the invention to access the bottle liquid cap 3 or the nose cavity mask 4. When the actuator button 30 is depressed and the valve assembly exerts downward force onto the dispensing nozzle 10 it releases gas and allows it to flow into the nose cavity mask 4 when a user's nose is placed within. Any appropriate valve structure will work as is known in the art. Additionally, the connector ring 31 can consist of a plastic or rubber ring that is designed into the bottle 1 or on the gas canister 9.

Figure 21:
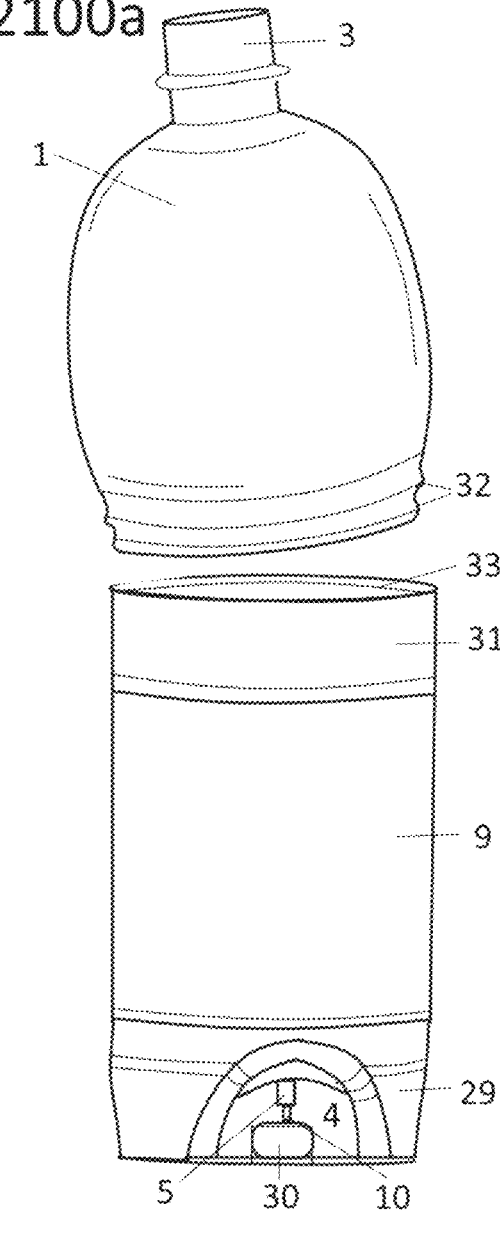
FIG. 21 shows the embodiment of the invention with the liquid container detached from the lower gas canister with connection ring with attachment ridges on the water bottle that join with the interior surface of the connection ring attached to the gas canister.

Referring to FIG. 21 outlines a portable liquid container 1 shown as 2800 that is detached from the connector ring 31 that is affixed to the gas canister 9 bottom unit using locking ridges 32 that fit into inner ridges 33 on the inner surface of the connector ring 31 to connect the portable liquid container and canister. All other explanations are the same as in FIG. 20.

Figure 22:
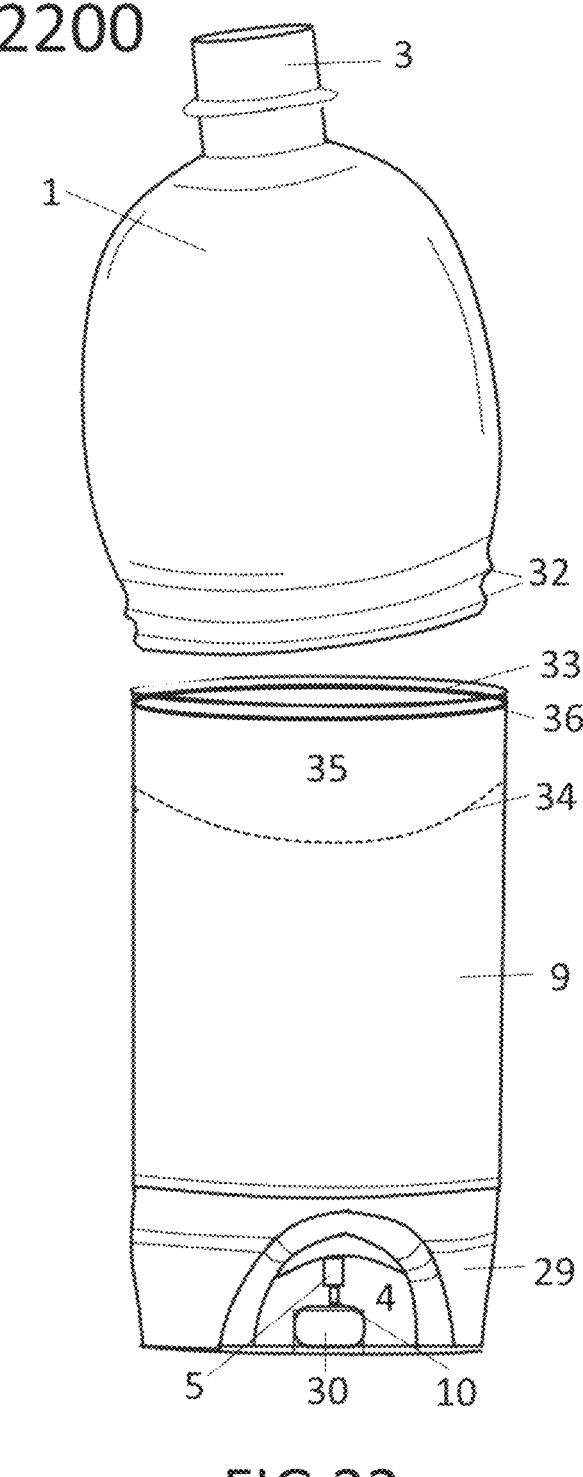
FIG. 22 shows the embodiment of the invention with the liquid container detached from the lower gas canister without the connection ring and with the gas canister bottom able to house the liquid container ridges by having an attachment ridge incorporated into the bottom of the gas canister.

Referring to FIG. 22 outlines a portable liquid container 1 shown as 2900 that is detached from the gas canister 9 bottom unit without connector ring but with gas canister 9 utilizing a connection lip 36 built into the leading edge of the bottom of gas canister 9 with inner ridges 33 in the inner body of the gas canister to enable it to hold the portable liquid container 1 snugly. The aerosol dome 34 is situated inferiorly to allow enough locking space 35 to accommodate the locking ridges 32 of the portable liquid container 1. All other explanations are the same as FIG. 20.

Although the instant invention has been described in relation to particular embodiments thereof, many other variations and modifications and other uses will become apparent to those skilled in the art.

What is claimed is:

1. A reusable container for storing and dispensing a liquid and a gas to a user comprising:
    a portable liquid container assembly, comprising:
        a portable liquid container;
        a liquid dispensing cap attached to an upper portion of said portable liquid container; whereby a liquid disposed within said portable liquid container is selectively dispensed or sealed off; and
        a first attachment mechanism structure;
    a gas canister assembly, comprising:
        a gas canister disposed on said portable liquid container;
        a lid cover that at least partially covers the gas canister having a hinge connection at one end;
        a nose cavity portion, disposed on said lid cover and shaped to fit a user nose, to facilitate delivery of a gas;
        a valve assembly disposed between said lid cover and said gas container wherein said gas is selectively dispensed and regulated through said lid cover when placed in a gas delivery orientation; and
        a second attachment mechanism structure; and
    wherein the first attachment mechanism structure and second attachment mechanism structure are releasably connected with each other to couple the portable liquid container assembly and gas canister assembly in an adjacently disposed arrangement.

2. The reusable container according to claim 1 wherein said first attachment mechanism structure and said second attachment mechanism structure comprise a pair of oriented appendages and a cavity floor.

3. The reusable container according to claim 1 wherein said second attachment mechanism structure is an attachment pin disposed on said gas canister and said first attachment mechanism structure is an attachment housing disposed on said portable liquid container wherein said attachment pin removably fits within said attachment housing.

4. The reusable container according to claim 1 wherein said first attachment mechanism structure is an adjustable attachment strap that elastically fits around said portable liquid container and includes a strap buckle that adjusts to connect said portable liquid container to said gas canister.

5. The reusable container according to claim 1 wherein said portable liquid container is made of a flexible material.

6. The reusable container according to claim 5 further comprising a flexible body cavity wherein said gas canister removably fits within said flexible body cavity.

7. The reusable container according to claim 5 wherein said flexible material is at least one selected from the group consisting of polyethylene, neoprene, and silicone.

8. The reusable container according to claim 5 wherein said flexible material is impregnated with anti-fowling and/or anti-bacterial compounds.

9. The reusable container according to claim 1 wherein said lid cover is a dual-purpose lid cover.

10. The reusable container according to claim 1 wherein the first attachment mechanism structure is a female attachment mechanism.

11. The reusable container according to claim 10 wherein the second attachment mechanism structure is a male attachment mechanism.

12. The reusable container according to claim 1 wherein the first attachment mechanism structure is a part of the liquid dispensing cap.

13. The reusable container according to claim 1 wherein the first attachment mechanism structure extends from a wall of the portable liquid container.

14. The reusable container according to claim 1 wherein the portable liquid container assembly includes: a portable liquid container with a neck; and a base structure with annular opening that is located around the neck between the portable liquid container and the liquid dispensing cap.

15. The reusable container according to claim 14 wherein the first attachment mechanism structure at least partially includes the base structure.

* * * * *